US007100602B2

(12) United States Patent (10) Patent No.: US 7,100,602 B2
Cole et al. (45) Date of Patent: Sep. 5, 2006

(54) SELF-DEFENSE FLASHLIGHT EQUIPPED WITH AN AEROSOL DISPENSER

(75) Inventors: Dennis Cole, Cardiff By The Sea, CA (US); Michael J. Skellern, Newport Coast, CA (US)

(73) Assignee: Shield Defense Technologies, Inc., Costa Mesa, CA (US)

( * ) Notice: Subject to any disclaimer, the term of this patent is extended or adjusted under 35 U.S.C. 154(b) by 90 days.

(21) Appl. No.: 10/851,717

(22) Filed: May 21, 2004

(65) Prior Publication Data

US 2005/0092320 A1 May 5, 2005

Related U.S. Application Data

(60) Provisional application No. 60/515,547, filed on Oct. 30, 2003.

(51) Int. Cl.
*A61M 11/00* (2006.01)
*B67D 5/14* (2006.01)
*B67D 1/07* (2006.01)
*F21V 33/00* (2006.01)
*F21V 25/00* (2006.01)

(52) U.S. Cl. ............................ 128/200.14; 128/200.1; 128/200.12; 128/200.21; 128/200.23; 128/202.16; 128/202.17; 128/203.23; 128/204.22; 222/62; 222/192; 362/96; 362/158; 362/259

(58) Field of Classification Search ........... 128/200.14, 128/200.11, 200.12, 200.21, 200.23, 202.16, 128/202.17, 203.23, 204.22
See application file for complete search history.

(56) References Cited

U.S. PATENT DOCUMENTS 2,855,497 A * 10/1958 Bacon ......................... 362/96
3,716,170 A * 2/1973 Mangels ..................... 222/162
3,776,429 A * 12/1973 DeLucia ..................... 222/162
RE28,537 E * 9/1975 Vickers, III ................. 222/192
4,184,196 A * 1/1980 Moret et al. .................. 433/29
4,186,851 A * 2/1980 Cantor ....................... 222/113
4,223,804 A * 9/1980 Morris et al. .................. 222/3
4,247,844 A * 1/1981 Zapolski et al. ............ 340/321
4,680,682 A * 7/1987 Parker ........................ 362/158
5,086,377 A * 2/1992 Roberts ...................... 362/102
5,243,376 A * 9/1993 Yokonuma .................. 396/201
5,254,379 A 10/1993 Kotsiopoulos et al. ..... 428/35.7
5,307,249 A * 4/1994 Vanwynsberghe ............ 362/96
5,331,523 A * 7/1994 Delzer ......................... 362/96
5,349,506 A * 9/1994 Maglica ...................... 362/158
5,349,507 A * 9/1994 Parker ........................ 362/158
5,373,427 A * 12/1994 McLean ...................... 362/96
5,420,766 A * 5/1995 Hollis ......................... 362/96
5,446,985 A * 9/1995 Chen .......................... 42/1.08
D383,234 S * 9/1997 Smith .......................... D26/49
5,673,819 A * 10/1997 Brunswig ................... 222/113
5,683,168 A * 11/1997 Teig et al. .................... 362/96

(Continued)

*Primary Examiner*—Henry Bennett
*Assistant Examiner*—Nihir Patel
(74) *Attorney, Agent, or Firm*—Stetina Brunda Garred & Brucker

(57) ABSTRACT

A flashlight for dispensing a substance from an aerosol canister includes an elongated housing having a front end, a rear end, and a central longitudinal axis, the aerosol canister being slidably received within the housing. The flashlight also includes at least one light emitting diode disposed approximate the front end of the housing and an elongated spray tube having a proximal end and a distal end, the proximal end being connected to the aerosol canister and the spray tube extending parallel to the central longitudinal axis such that the distal end extends beyond the front end of the housing.

21 Claims, 4 Drawing Sheets

U.S. PATENT DOCUMENTS

| | | | | | |
|---|---|---|---|---|---|
| 5,795,054 | A | * | 8/1998 | Booty, Jr. | 362/96 |
| 5,806,961 | A | * | 9/1998 | Dalton et al. | 362/183 |
| 5,909,062 | A | * | 6/1999 | Krietzman | 307/64 |
| 5,941,629 | A | * | 8/1999 | Tuscher | 362/253 |
| 6,007,219 | A | * | 12/1999 | O'Meara | 362/259 |
| 6,736,523 | B1 | * | 5/2004 | Alvey | 362/158 |
| 2004/0223342 | A1 | * | 11/2004 | Klipstein et al. | 362/555 |

* cited by examiner

SELF-DEFENSE FLASHLIGHT EQUIPPED WITH AN AEROSOL DISPENSER

CROSS-REFERENCE TO RELATED APPLICATION

This application claims priority to copending U.S. provisional application entitled, "Laser and Tear Gas Equipped Self-defense LED Flashlight," having Ser. No. 60/515,547, filed Oct. 30, 2003, which is entirely incorporated herein by reference.

TECHNICAL FIELD

The present disclosure relates generally to self-defense equipment. More specifically, the present disclosure relates to a self-defense flashlight equipped with an aerosol dispenser.

BACKGROUND

Threats to personal safety cover a broad spectrum of potential injury and/or lethality to individuals, for example, ranging from simple assault to loss of life. Weapons such as pistols, rifles, and other firearms are often useful as self-defense devices. The use of these weapons, however, is not always appropriate for self-defense in that the potential for death or serious bodily injury may often far outweigh the potential injury to the user that feels threatened. As such, it is apparent that varying levels of non-lethal force alternatives are needed to respond to varying levels of potential danger.

Law enforcement officers, military personnel, etc., often find it necessary to rely on non-lethal force to properly perform their duties. For example, acts such as dispersing protestors or riotous crowds seldom, if ever, requires a use of lethal force. Unfortunately, existing non-lethal force devices are typically maintained in the patrol car, vehicle, etc., in which the enforcement personnel travel, making them somewhat inaccessible. Moreover, the use of a non-lethal device that is readily available to a law enforcement official could actually prevent the official from having to rely on unholstering and potentially discharging a firearm. Instances of the use of lethal force often lead to lost time on the job for the concerned official and legal costs for his employer due to legal action stemming from the use of force. These issues can potentially be avoided with the use of non-lethal force.

Individuals also have an interest in the use of non-lethal self-defense devices. Although many individuals can gain access to firearms and other potentially lethal devices, such devices are often not readily available to others. Moreover, as in the case of law enforcement officials, the use of firearms and other lethal devices is not always commensurate with the level of harm the individual faces. Also, some individuals do not feel capable of, or properly trained to, use lethal devices in their defense. Also, some individuals do not believe the use of lethal force is appropriate in that there is the potential for injuring and/or killing innocent individuals, such as family members residing in the same residence.

Therefore, there is a need for improved non-lethal self-defense equipment which addresses these and other shortcomings of the prior art.

SUMMARY

Briefly described the present disclosure relates a flashlight for dispensing a substance from an aerosol canister. An embodiment of the flashlight includes an elongate housing having a front end, a rear end, and a central longitudinal axis, the aerosol canister being slidably received within the housing. The flashlight also includes at least one light emitting diode disposed approximate the front end of the housing and an elongated spray tube having a proximal end and a distal end. The proximal end of the spray tube is connected to the aerosol canister and the spray tube extends parallel to the central longitudinal axis such that the distal end extends beyond the front end of the housing.

A further embodiment of a flashlight for dispensing a substance from an aerosol canister includes an elongate housing having a front end and a rear end, the aerosol canister being slidably received within the housing. The flashlight also includes a light source disposed adjacent the front end of the housing and a spray tube having a proximal end and a distal end. The proximal end is connected to the aerosol canister and the distal end extends beyond the front end of the housing such that the substance can be discharged therefrom in a desired direction. A laser diode disposed approximate the front end of the housing is arranged to emit a laser in the desired direction of discharge.

Yet another embodiment of a flashlight for dispensing a substance from an aerosol canister includes an elongate housing having a front end and a rear end, the aerosol canister being slidably received within the housing. The flashlight also includes a light source disposed approximate the front end of the housing and a spray tube having a proximal end and a distal end. The proximal end is in fluid communication with the aerosol canister and the distal end extends beyond the front end of the housing. The flashlight further includes a switch assembly including a plunger extending into the housing, the plunger being configured to cause the substance in the aerosol canister to be emitted through the spray tube when the plunger is urged inwardly. A switch door is operable between an open and a closed position such that moving the switch door from the closed position to the open position allows a user to access the plunger.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the self-defense flashlight can be better understood with reference to the following drawings. The components in the drawings are not necessarily to scale, emphasis instead being placed upon clearly illustrating the principles of the self-defense flashlight. Moreover, in the drawings, like reference numerals designate corresponding parts throughout the several views.

DETAILED DESCRIPTION OF THE PREFERRED EMBODIMENT

Figure 1:
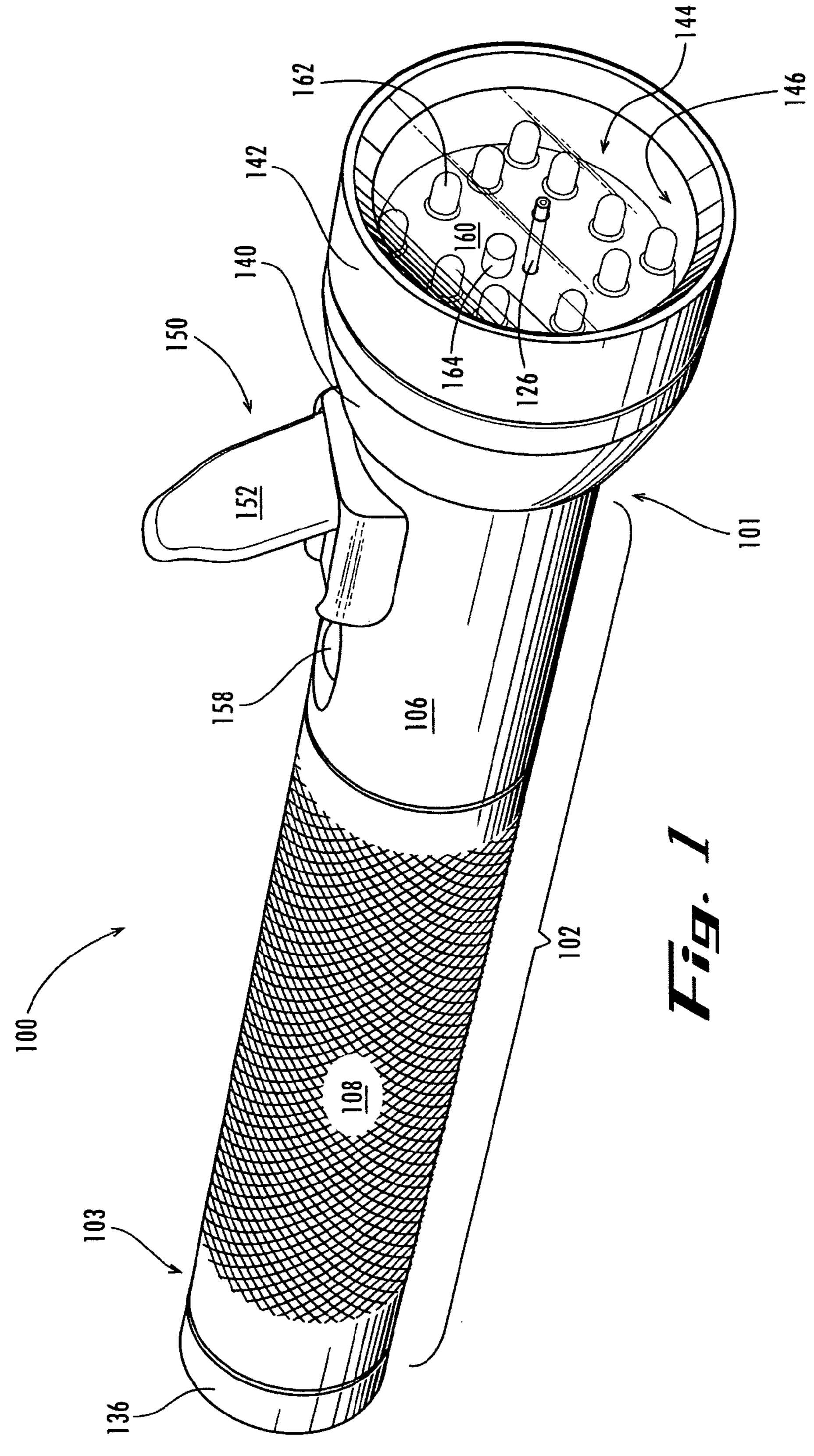
FIG. 1 is perspective view of a self-defense flashlight constructed in accordance with an embodiment of the present disclosure.

Reference will now be made in detail to the description of the self-defense flashlight as illustrated in the drawings. While the self-defense flashlight will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

In particular, FIG. 1 illustrates a non-lethal self-defense device, in the form of a flashlight 100. In its assembled state, visible components of the preferred embodiment of the flashlight 100 shown include an elongated housing 102 including a front housing 106 and a rear housing 108, a switch assembly 150 also located on the housing 102, a rear cap 136, located at the rear end 103 of the housing 102, and a head 140 located on the front end 101 of the housing 102.

Figure 2:
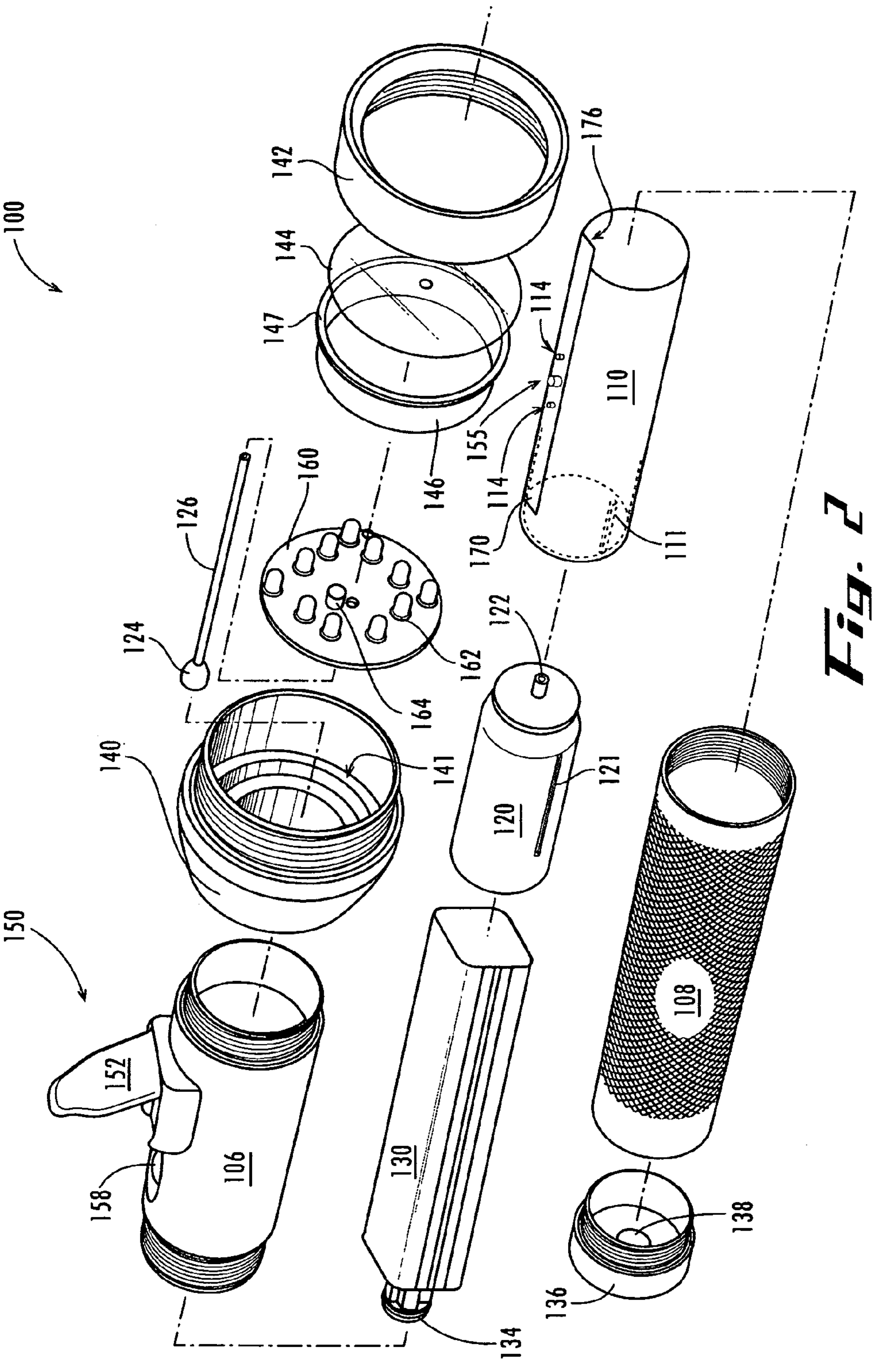
FIG. 2 is an exploded, perspective view of the self-defense flashlight as shown in FIG. 1.
Figure 3:
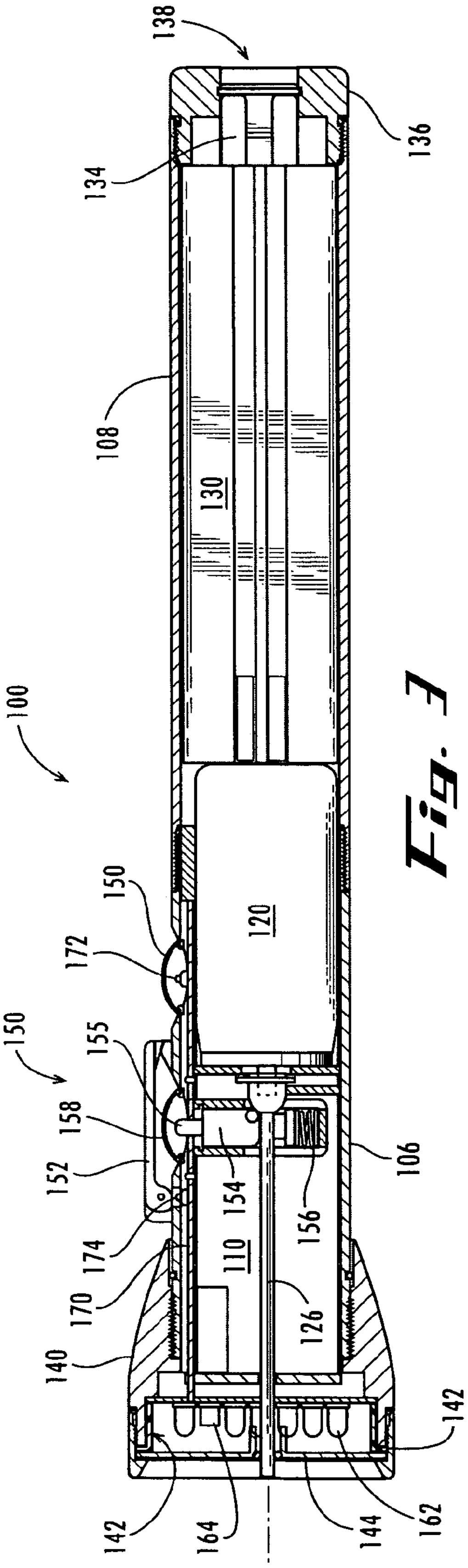
FIG. 3 illustrates a cross-sectional view of the self-defense flashlight as shown in FIG. 1.
Figure 4:
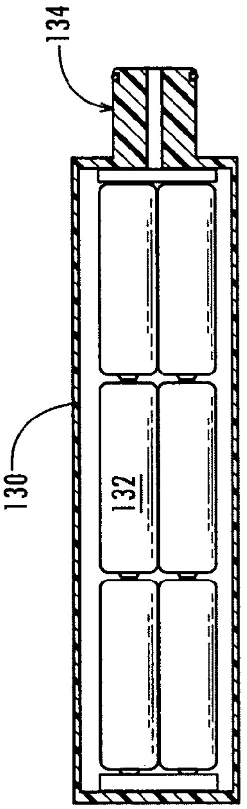
FIG. 4 illustrates a cross-sectional view of the battery housing as shown in FIG. 2.

Also located at the front end 101 of the housing 102 are the retainer 146 in the front cap 142. The retainer 146 is used to secure a first printed circuit board (PCB) 160 between a portion of the head 140 and the retainer 146 as the front cap is threadably attached to the head 140.Prior to securing the front cap 142 to the head 140, a lens 144 is placed adjacent a portion of the retainer 146 such that the lens 144 is secured in place between the front cap 142 and the retainer 146 such that the lens 144 is secured in place between the front cap 142 and the retainer 146 as the front cap is threadably attached to the head 140.The first PCB 160 preferably includes a plurality of light emitting diodes (LEDs) 162 and a laser diode 164. As well, both the first PCB 160 and lens 144 have apertures located therein such that a s pray tube 126 is permitted to extend through and beyond the lens 144. This configuration allows a user to expel a substance such as teargas, etc., from a canister 120 (FIG. 2) located within the flashlight 100 by way of the spray tube 126. The LEDs 162 and laser diode 164 receive power by way of a light circuit (not shown) located on the first PCB 160. Preferably, the laser diode 164 provides a visible laser that allows a user to aim the flashlight 100, and subsequently the discharge of the expelled substance from the canister 120 in the desired direction. Opening the switch door 152 of the switch assembly 150 allows the user to both energize the laser diode 164 and access the switch required to emit the substance held in the internal canister 120.

Referring now to FIGS. 2–5, a preferred embodiment of the flashlight 100 further includes a canister housing 110, a canister 120, a battery housing 130, a second printed circuit board 170, and the remaining components of the switch assembly 150. One embodiment of the flashlight 100, among others, includes a battery housing 130 enclosing a plurality of batteries 132, the batteries 132 being rechargeable by way of a charging port 134 at the base of the battery housing 130. Preferably, the battery housing 130 is slidably received within the rear housing 108 of the flashlight 110 such that the charging port 134 is accessible through a chargeable aperture 138 formed in the rear cap 136. As such, the batteries 132 may be charged by way of the charging port 134 without having to remove the battery housing 130 from the flashlight 110. However, rapid replenishment of the power source may be accomplished by removing the rear cap 136 from the rear housing 108, replacing the battery housing 130 containing the spent batteries 132 with a spare battery housing 130 with charged batteries 132, and threadably reattaching the rear cap 136 to the rear housing 108. Preferably, embodiments will be rechargeable from either 12 volt DC or 110 volt AC sources. Note also, embodiments are envisioned wherein a battery housing 130 is not required for containing the batteries 132, as well as embodiments wherein non-rechargeable batteries are used.

Figure 5:
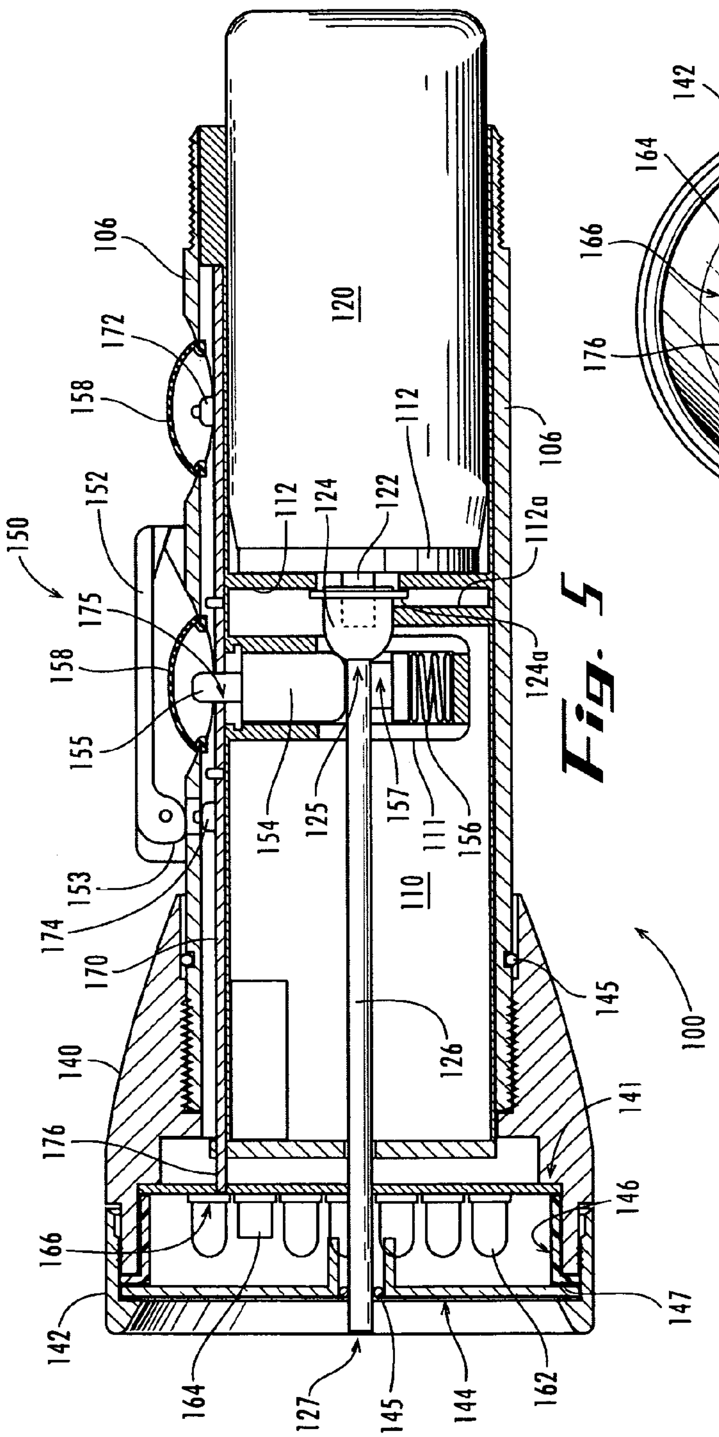
FIG. 5 illustrates a partial, cross-sectional view of the self-defense flashlight as shown in FIG. 1.
Figure 6:
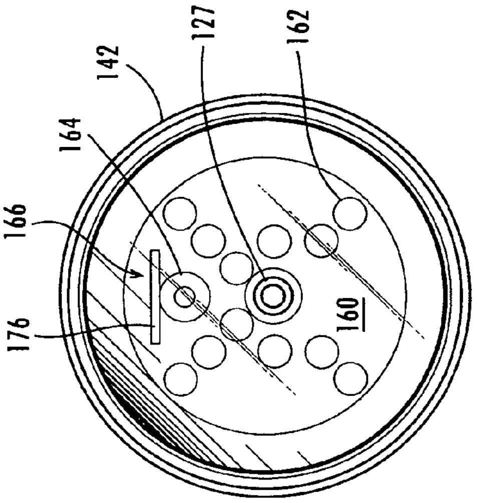
FIG. 6 illustrates a front view of the self-defense flashlight as shown in FIG. 1.

As best seen in FIG. 5, the canister 120 is slidably received within the canister housing 110, which is in turn slidably received within the front housing 106. Preferably, the canister 120 is a standard type aerosol canister including a nozzle 122 that when displaced from its at rest position causes the substance contained within the canister 120 to be discharged. A first ledge 112 and a second ledge **112*a* extend inwardly from the inner surface of the canister housing 110 such that a gap is formed therebetween. The spray tube mount 124 is positioned within the canister housing 110 such that a portion of the spray tube mount 124 is movably disposed within the gap between the first and second ledges 112 and 112*a*. As shown, the spray tube mount 124 includes a radially extending ledge 124*a* which is partially disposed in the gap. So positioned, the radially extending ledge 124*a* limits the amount of travel of the spray tube mount 124 to the width of the gap and maintains the spray tube mount 124 within the canister housing 110 as the canister 120 is inserted into and removed from the housing 110**.

As shown, the proximal end 125 of the spray tube 126 is secured to the spray tube mount 124 and the distal end 127 extends beyond the lens 144. The spray tube 126 extends through the plunger housing 111 portion of the canister housing 110 and under a portion of the plunger 154 which a user can cause to come into contact with the proximal end 125 of the spray tube 126 and/or the spray tube mount 124, as is discussed in greater detail hereinafter. A canister 120 is inserted into the canister housing 110 until the front portion of the canister 120 comes into contact with the first ledge 112. As the canister 120 is inserted, the nozzle 122 is slidably received within the spray tube mount 124 which is held in position by the interaction of the radially extending ledge **124*a*** within the gap.

Preferably, a switch assembly 150 includes a switch door 152 having a camming surface 153, a plunger 154 including a button 155, and a spring 156. To prevent inadvertent discharge of substances from the canister 120, the switch door 152 is provided and is normally maintained in a closed position, thereby preventing the inadvertent depression of the plunge 154 and subsequent discharge of substance from the canister 120. The switch door 152 includes a camming surface 153 that is configured to contact laser switch 174 as the switch door 152 is moved from the closed to the open position. Contact of the camming surface 153 with the laser switch 174 provides power to the laser diode 164, which in turn emits a visible laser for aiming the flashlight 110. Similarly, when a user contacts a light switch 172, power is provided to the LEDs 162 on the first PCB 160, thereby causing illumination as desired. After a user has placed the switch door 152 in the open position, the user now has access to the button 155 which is used to urge the plunger 154 inwardly so as to contact the proximal end 125 of the spray tube 126 and/or the spray tube mount 124. Preferably, the plunger has a central portion 157 which allows the spray tube to pass through the plunger 154 in an uninhibited manner, unless the plunger 154 is being urged inwardly by a user. As well, a spring 156 is placed between a plunger housing 111 and the bottom of the plunger 154 such that the plunge 154 is urged outwardly when no pressure is being exerted on the button 155 by a user.

Preferably, a second printed circuit board (PCB) 170 is secured to the upper portion of the canister housing 110. A pair of projections 114 on the upper portion of the canister housing 110 mate with matching apertures on the second PCB 170 to insure proper alignment. The second PCB 170 preferably includes a light switch 172, a laser switch 174, a button aperture 175, and a plug 176. The button aperture 175 allows the button 155 of the plunger 154 to pass through the second PCB 170 so as to be accessible by a user. The plug 176 is configured to mate with a socket 166 formed in the first PCB 160, thereby connecting the circuits on the first and second PCBs 160, 170.

Preferably, a switch assembly 150 includes a switch door 152 having a camming surface 153, a plunger 154 including a button 155, and a spring 156. To prevent inadvertent discharge of substances from the canister 120, the switch door 152 is provided and is normally maintained in a closed position, thereby preventing the inadvertent depression of the plunger 154 and subsequent discharge of substance from the canister 120. The switch door 152 includes a camming surface 153 that is configured to contact laser switch 174 as the switch door 152 is moved from the closed to the open position. Contact of the camming surface 153 with the laser switch 174 provides power to the laser diode 164, which in turn emits a visible laser for aiming the flashlight 110. Similarly, when a user contacts a light switch 172 power is provided to the LEDs 162 on the first PCB 160, thereby causing illumination as desired. After a user has placed the switch door 152 in the open position, the user now has access to the button 155 which is used to urge the plunger 154 inwardly so as to contact the proximal end 125 of the spray tube 126 and/or the spray tube mount 124. Preferably, the plunger has a central portion 157 which allows the spray tube to pass through the plunger 154 in an uninhibited manner, unless the plunger 154 is being urged inwardly by a user. As well, a spring 156 is placed between a plunger housing 111 and the bottom of the plunger 154 such that the plunger 154 is urged outwardly when no pressure is being exerted on the button 155 by a user.

Operation of the flashlight 110 for use as a source of illumination requires a user to operate the light switch 172. The user presses down on the flexible boot 158, thereby eventually exerting pressure on the light switch. Activation of the light switch 172 provides power to the LEDs 162, causing them to illuminate. To turn off power to the LEDs 162, the user merely depresses the light switch 172 again.

As previously noted, discharging substances from the canister 120 preferably requires that a protective switch door 152 be moved from a closed to an open position, thereby giving the user access to the plunger 154. As the switch door 152 is moved to the open position, the camming surface 153 contacts the laser switch 174, thereby causing the laser diode 164 to emit a visible laser. The visible laser can be used for aiming the flashlight 110, as well as a psychological deterrent to a would be assailant. To discharge the substances contained in the canister 120 the user exerts pressure on the flexible boot 158, and in turn on the button 155 of the plunger 154. As the plunger 154 is urged inwardly a portion of the plunger eventually comes into contact with a surface on the spray tube mount 124, which causes the spray tube mount 124 to move rearwardly thereby exerting force on the nozzle 122.

Eventually, enough force is exerted on the nozzle 122 to cause the release of the substance within the canister 120. The substance is then discharged through the spray tube 126 which lies along the central longitudinal axis of the flashlight 100, and out the distal end 127 of the spray tube 126. Note, the use of LEDs 162 rather than an incandescent bulb type configuration for illumination allows the configuration wherein the spray tube 126 lies approximately along the central longitudinal axis of the flashlight 100. After a desired amount of substance has been discharged from the canister 120, a user merely ceases to exert pressure on the button 155 of the plunger 154, thereby allowing the spring 156 to urge the plunger 154 outwardly and away from the spray tube mount 124. As pressure is released from the spray tube mount 124, the nozzle 122 returns to its at rest position, thereby causing discharge of the substance to cease.

It should be emphasized that the above-described embodiments of the present self-defense flashlight, particularly, any "preferred" embodiments, are merely possible examples of implementations, merely set forth for a clear understanding of the principles of the self-defense flashlight. Many variations and modifications may be made to the above-described embodiment(s) of the self-defense flashlight without departing substantially from the spirit and principles of the self-defense flashlight. All such modifications and variations are intended to be included herein within the scope of this disclosure and the self-defense flashlight and protected by the following claims.

Therefore, having thus described the invention, at least the following is claimed:

1. A flashlight for dispensing a substance from an aerosol canister, the flashlight comprising:

an elongated housing having a front end, a rear end, and a central longitudinal axis, the aerosol canister being slidably received within the housing;

at least one light emitting diode disposed approximate the front end of the housing;

an elongated spray tube having a proximal end and a distal end, the proximal end being connected to the aerosol canister and the spray tube extending parallel to the central longitudinal axis such that the distal end extends beyond the front end of the housing;

a canister housing having a projection extending inwardly from an inner surface of the canister housing, the canister housing being configured to slidably receive the aerosol canister; and wherein the aerosol canister includes a mating groove configured to receive the projection as the aerosol canister is slidably disposed in the canister housing, the canister housing being configured to be received within the housing.

2. The flashlight of claim 1, further comprising a laser diode disposed approximate the front end of the housing, the laser diode being arranged to emit a laser parallel to the central longitudinal axis of the housing.

3. The flashlight of claim 2, further comprising:

a first printed circuit board disposed approximate the front end of the housing, the first printed circuit board including a light circuit; and wherein the at least one light emitting diode further includes a plurality of light emitting diodes, the plurality of light emitting diodes and the laser diode being disposed on the first printed circuit board, the distal end of the spray tube extending through and beyond the first printed circuit board.

4. The flashlight of claim 3, further comprising:

a lens secured to the front end of the housing such that the light emitting diodes and laser diode are disposed between the first printed circuit board and the lens; and wherein the distal end of the spray tube extends through and beyond the lens.

5. A flashlight for dispensing a substance from an aerosol canister, the flashlight comprising;

an elongated housing having a front end, a rear end, and a central longitudinal axis, the aerosol canister being slidably received within the housing;

at least one light emitting diode disposed approximate the front end of the housing;

a laser diode disposed approximate the front end of the housing, the laser diode being arranged to emit a laser parallel to the central longitudinal axis of the housing;

an elongated spray tube having a proximal end and a distal end, the proximal end being connected to the aerosol canister and the spray tube extending parallel to the central longitudinal axis such that the distal end extends beyond the front end of the housing; and a switch assembly disposed on the housing, the switch assembly including:

a plunger extending into the housing, the plunger being configured to displace the proximal end of the spray tube when urged inwardly such that the substance in the aerosol canister is emitted through the spray tube;

a switch door operable between an open and a closed position, the switch door including a camming surface; and wherein moving the switch door from the closed position to the open position causes the camming surface to activate a laser switch, thereby providing power to and activating the laser diode.

6. The flashlight of claim 1, further comprising:

a canister housing, the canister housing including a projection extending inwardly from an inner surface of the canister housing, the canister housing being configured to slidably receive the aerosol canister; and wherein the aerosol canister includes a mating groove configured to receive the projection as the aerosol canister is slidably disposed in the canister housing, the canister housing being configured to be received within the housing.

7. The flashlight of claim 1, further comprising a rechargeable power source disposed within the housing, the housing including a charging port such that the power source is rechargeable while being disposed in the housing.

8. A flashlight for dispensing a substance from an aerosol canister, the flashlight comprising:

an elongated housing having a front end and a rear end, the aerosol canister being slidably disposed in the housing;

the housing further including a projection extending inwardly from an inner surface of the housing, and wherein the aerosol canister further includes a mating groove configured to receive the projection as the aerosol canister is slidably disposed in the housing;

a light source disposed adjacent the front end of the housing;

a spray tube having a proximal end and a distal end, the proximal end being connected to the aerosol canister and the distal end extending beyond the front end of the housing such that the substance can be discharged therefrom in a desired direction; and a laser diode disposed approximate the front end of the housing, the laser diode being arranged to emit a laser in the desired direction of discharge.

9. The flashlight of claim 8, wherein the light source further comprising a plurality of light emitting diodes.

10. The flashlight of claim 9, further comprising a rechargeable power source disposed within the housing, the housing including a charging post such that the power source is rechargeable while being disposed in the housing.

11. The flashlight of claim 9, further comprising:

a first printed circuit board disposed adjacent the front end of the housing, the first printed circuit board including a light circuit; and wherein the plurality of light emitting diodes and the laser diode are disposed on the first printed circuit board, and the distal end of the spray tube extends through and beyond the first printed circuit board.

12. The flashlight of claim 11, further comprising:

a lens secured to the front end of the housing such that the light emitting diodes and the laser diode are disposed between the first printed circuit board and the lens; and wherein the distal end of the spray tube extends through and beyond the lens.

13. A flashlight for dispensing a substance from an aerosol canister, the flashlight comprising:

an elongated housing having a front end and a rear end, the aerosol canister being slidably received within the housing;

a light source disposed adjacent the front end of the housing;

a spray tube having a proximal end and a distal end, the proximal end being connected to the aerosol canister and the distal end extending beyond the front end of the housing such that the substance can be discharged therefrom in a desired direction;

a laser diode disposed approximate the front end of the housing, the laser diode being arranged to emit a laser in the desired direction of discharge; and a switch assembly disposed on the housing, the switch assembly including:

a plunger extending into the housing, the plunger being configured to contact the proximal end of the spray tube when urged inwardly such that the substance in the aerosol canister is emitted through the spray tube;

a switch door operable between an open and a closed position;

wherein moving the switch door from the closed position to the open position allows user access to the plunger; and the switch door further comprises a camming surface, the canning surface being configured to contact a laser switch as the switch door is moved from the closed to the open position, thereby providing power to the laser diode.

14. The flashlight of claim 13, further including a laser switch, and wherein the switch door further comprises a camming surface, the camming surface being configured to contact the laser switch as the switch door is moved from the closed to the open position, thereby providing power to the laser diode.

15. The flashlight of claim 8, wherein the housing further includes a projection extending inwardly from an inner surface of the housing, and wherein the aerosol canister further includes a mating groove configured to receive the projection as the aerosol canister is slidably disposed in the housing.

16. A flashlight for dispensing a substance from an aerosol canister, the flashlight comprising:

an elongated housing having a front end and a rear end, the aerosol canister being slidably received within the housing;

a light source disposed approximate the front end of the housing;

a spray tube having a proximal end and a distal end, the proximal end being in fluid communication with the aerosol canister and the distal end extending beyond the front end of the housing;

a canister housing, the canister housing including means for aligning the aerosol canister disposed on an inner surface of the canister housing, the canister housing being configured to slidably receive the aerosol canister;

wherein the aerosol canister includes a mating means for aligning the aerosol canister configured to receive the means for aligning as the aerosol canister is slidably disposed in the canister housing; and a switch assembly including:

a plunger extending into the housing, the plunger being arranged and configured to cause the substance in the aerosol canister to be emitted through the spray tube when the plunger is urged inwardly;

a switch door operable between an open and a closed position; and wherein moving the switch door from the closed position to the open position allows a user to access the plunger.

17. The flashlight of claim 16, further comprising a laser diode disposed approximate the front end of the housing, the laser diode being arranged to emit a laser parallel to the central longitudinal axis of the housing.

18. The flashlight of claim 17, further including a laser switch and wherein the switch door further includes a camming surface configured to activate the laser switch as the switch door is moved from the closed to the open position, thereby providing power to the laser diode.

19. The flashlight of claim 16, wherein the light source further comprises a plurality of light emitting diodes.

20. The flashlight of claim 19, further comprising:

a first printed circuit board disposed approximate the front end of the housing, the first printed circuit board including a light circuit; and wherein the plurality of light emitting diodes and the laser diode are disposed on the first printed circuit board, and the distal end of the spray tube extends through and beyond the first printed circuit board.

21. The flashlight of claim 16, further comprising:

a canister housing, the canister housing including means for aligning the aerosol canister disposed on an inner surface of the canister housing, the canister housing being configured to slidably receive the aerosol canister; and wherein the aerosol canister includes a mating means for aligning the aerosol canister configured to receive the means for aligning as the aerosol canister is slidably disposed in the aerosol housing.

* * * * *